(12) United States Patent
Ragsdale et al.

(10) Patent No.: US 6,771,082 B2
(45) Date of Patent: Aug. 3, 2004

(54) RESISTANCE CIRCUIT STABILIZATION AND PULSE DURATION CONTROL SYSTEMS FOR ELECTROPORATION INSTRUMENTS

(75) Inventors: Charles W. Ragsdale, Concord, CA (US); Tony Chiu, San Leandro, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 61 days.

(21) Appl. No.: 10/313,951

(22) Filed: Dec. 6, 2002

(65) Prior Publication Data

US 2003/0139889 A1 Jul. 24, 2003

Related U.S. Application Data

(60) Provisional application No. 60/337,103, filed on Dec. 6, 2001.

(51) Int. Cl.[7] .................. G01R 27/02; G01R 27/26; A61B 18/12; C12M 1/32
(52) U.S. Cl. .................. 324/711; 324/692; 324/677; 606/34; 435/285.2
(58) Field of Search .................. 324/710, 711, 324/692, 707, 677, 681; 435/285.2, 461; 606/32–42

(56) References Cited

U.S. PATENT DOCUMENTS

| | | | | |
|---|---|---|---|---|
| 4,750,100 A | | 6/1988 | Ragsdale | 363/86 |
| 4,946,793 A | * | 8/1990 | Marshall, III | 435/285.2 |
| 5,504,434 A | * | 4/1996 | Schepis et al. | 324/719 |
| 5,642,035 A | | 6/1997 | Ragsdale | 323/282 |
| 5,656,926 A | | 8/1997 | Ragsdale | 323/282 |
| 6,051,422 A | | 4/2000 | Kovacs et al. | 435/287.1 |
| 6,258,592 B1 | * | 7/2001 | Ragsdale et al. | 435/285.2 |
| 6,398,779 B1 | * | 6/2002 | Buysse et al. | 606/34 |
| 6,423,057 B1 | * | 7/2002 | He et al. | 606/34 |

OTHER PUBLICATIONS

Copy of Notification of Transmittal of the International Search Report or the Declaration dated Nov. 14, 2003.

* cited by examiner

*Primary Examiner*—Anjan K. Deb
(74) *Attorney, Agent, or Firm*—Gerald T. Gray, Esq.; Townsend and Townsend and Crew LLP (57) ABSTRACT

Systems, methods and apparatus for stabilizing resistance measurements in electroporation systems so as to achieve high-accuracy measurements, and for controlling the pulse duration, or time constant, of electroporation pulses. Circuitry is provided to accurately determine the resistance of a sample in the electroporation system, for example a sample provided in an electroporation cuvette. Additionally, a resistance control system is provided to automatically measure the resistance of a sample, determine a capacitance and determine a parallel add-on resistance that substantially provides a desired pulse duration (time constant) for an electroporation pulse.

17 Claims, 12 Drawing Sheets

RESISTANCE CIRCUIT STABILIZATION AND PULSE DURATION CONTROL SYSTEMS FOR ELECTROPORATION INSTRUMENTS

CROSS-REFERENCES TO RELATED APPLICATIONS

This application claims the benefit of U.S. Provisional Patent Application Serial No. 60/337,103, titled "RESISTANCE CIRCUIT STABILIZATION AND PULSE DURATION, CONTROL SYSTEMS FOR ELECTROPORATION INSTRUMENTS", filed Dec. 6, 2001, which is hereby incorporated by reference in its entirety.

BACKGROUND OF THE INVENTION

The present invention relates generally to electroporation systems and more particularly to systems and methods for stabilizing resistance measurements and for controlling the duration of applied electrical pulses in electroporation systems.

It is known that exposure of cells to intense electric fields for brief periods of time temporarily destabilized membranes. This effect has been described as a dielectric breakdown due to an induced transmembrane potential, and has been termed "electroporation". A variety of procedures use electroporation treatments including production of monoclonal antibodies, cell-cell fusion, cell-tissue fusion, insertion of membrane proteins, and genetic transformation. Protocols for the use of electroporation to load cells in vitro typically use a suspension of single cells or cells that are attached in a planar manner to a growth surface. In vivo electroporation is more complex because tissues are involved. Tissues are composed of individual cells that collectively make up a three-dimensional structure. In either case, the effects on the cell are generally the same.

The cells or tissue are exposed to electric fields by administering one or more direct current pulses. Electrical treatment is conducted in a manner that results in a temporary membrane destabilization with minimal cytotoxicity. The intensity of electrical treatment is typically described by the magnitude of the applied electric field. This field is defined as the voltage applied to the electrodes divided by the distance between the electrodes. Electric field strengths ranging from 1000 to 5000 V/cm are typically used for delivering molecules in vivo and are also specific to the cells or tissue under investigation.

U.S. Pat. Nos. 6,258,592, 5,729,426, 5,656,926, 5,642,035, and 4,750,100, each of which are hereby incorporated by reference in its entirety, disclose examples of electroporation systems and various subsystems such as voltage control subsystems. In a typical electroporation system, an internal charge reservoir (e.g., a capacitor) stores electric energy (charge). A high-voltage switch couples the charge reservoir to a sample cuvette containing cells to be electroporated, and the stored charge discharges into the sample, typically as one or more pulses. Pulses are usually exponentially decaying in shape; however, square waves have also been used. The duration of each pulse is called pulse width. Molecule loading has been performed with pulse widths ranging from microseconds ($\mu s$) to milliseconds (ms). Typically, one or multiple pulses are utilized during electrical treatment.

One problem is that the sample can have a wide range of resistance values, however, the electroporation effect may have a narrow range of parameters, e.g., pulse voltage and pulse duration, for which efficiency is highest. There is a narrow gap between electroporation and electrocution; if a pulse has too long a duration or too high a field strength, the cells may be lysed (destroyed). Minimal conditions tend to reduce the efficiency of electroporation. It is, therefore, desirable to provide systems and methods for controlling the pulse duration, or time constant, of electroporation pulses.

It is also generally desirable to apply an appropriate voltage to the sample so as to not damage the sample. Thus, it is important to accurately determine the resistance of the sample. Methods and apparatus for measuring resistance in electroporation systems and correcting for the series protection resistor are disclosed in U.S. Pat. Nos. 5,729,426, 5,642,035, and 5,656,926, each previously incorporated by reference in its entirety for all purposes. However, the resistance-measuring circuits as disclosed therein require sufficient stability of a coupling capacitor to achieve high-accuracy measurements.

Accordingly, it is desirable to provide systems, methods and apparatus for stabilizing resistance measurements in electroporation systems to achieve high-accuracy measurements and to provide systems and methods for controlling the pulse duration, or time constant, of electroporation pulses.

BRIEF SUMMARY OF THE INVENTION

The present invention provides systems, methods and apparatus for stabilizing resistance measurements in electroporation systems so as to achieve high-accuracy measurements. The present invention also provides systems, methods and apparatus for controlling the pulse duration, or time constant, of electroporation pulses.

According to the present invention, circuitry is provided to accurately determine the resistance of a sample in the electroporation system, for example a sample provided in an electroporation cuvette. Additionally, a resistance control system is provided to automatically measure the resistance of a sample, determine a capacitance and determine a parallel add-on resistance that substantially provides a desired pulse duration (time constant) for an electroporation pulse.

According to an aspect of the invention, a method is provided for applying an electrical pulse to a sample for a desired duration. The method typically includes identifying a desired pulse duration, automatically measuring the resistance Rs of the sample, automatically selecting a capacitance C to be placed in series with the sample, and automatically determining a resistance R2 to be placed in parallel with the sample such that a time constant $T=C \times R$ is substantially equal to the desired pulse duration, wherein $R=(Rs \times R2)/(Rs+R2)$. In certain aspects, R2 may be implemented using a single resistor or a multiple resistor arrangement, however, R2 is generally a composite resistance that includes any resistance continuously within the circuit arrangement and any selected component or components. Similarly, C may be a composite capacitance including any capacitance continuously within the circuit arrangement and any selected component or components.

According to another aspect of the present invention, a method is provided for automatically determining the resistance of a sample in an electroporation system. The method typically includes applying a first input signal to the sample across a coupling capacitor and a drive resistor circuit, the first input signal having an input voltage Ein at a first frequency f1, the drive resistor circuit having a resistance R1, and measuring the voltage E1 across the sample at said first frequency. The method also typically includes applying a second input signal to the sample across the drive resistor circuit, the second input signal having the input voltage Ein at a second frequency f2, and measuring the voltage E2 across the sample at said second frequency. The method further typically includes determining the sample resistance Rs using Ein and the measured values E1 and E2 without using the capacitance of the coupling capacitor.

According to yet another aspect of the invention, a circuit arrangement is provided in an electroporation system configured to determine the resistance of a sample. The arrangement typically includes a signal source for providing a sinusoidal voltage signal to a sample across a coupling capacitor and drive resistor, a frequency switch coupled to the signal source, the switch configured to adjust the frequency of the voltage signal applied by the signal source, and a microprocessor coupled to the frequency switch, an output of the signal source and the sample. The microprocessor typically controls the signal source, via the frequency switch, to apply a first voltage signal to the sample at a first frequency and a second voltage signal to the sample at a second frequency, the first and second voltage signals having substantially the same voltage amplitude. The microprocessor is typically configured to determine the sample resistance Rs based on the applied voltage amplitude of the first and second voltage signals and on the detected voltage levels across the sample at the first and second frequencies without using the capacitance of the coupling capacitor.

Reference to the remaining portions of the specification, including the drawings claims and Appendices, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

DETAILED DESCRIPTION OF THE INVENTION

The present invention provides resistance measurement systems and methods for use in electroporation (transfection) systems to allow for correction for an internal protection resistor in the high-voltage delivery system of an electroporation device or system. An internal protection resistor is typically provided to protect the system's semiconductor controlled rectifiers (SCRs) in the high-joule switch from the large currents that can occur during an arc. A method of measuring resistance and correcting for the series protection resistor is the subject of U.S. Pat. Nos. 5,729,426, 5,642,035, and 5,656,926, which have previously been incorporated by reference. However, the previously used resistance-measuring circuits as disclosed therein require sufficient stability of a coupling capacitor.

Figure 1:
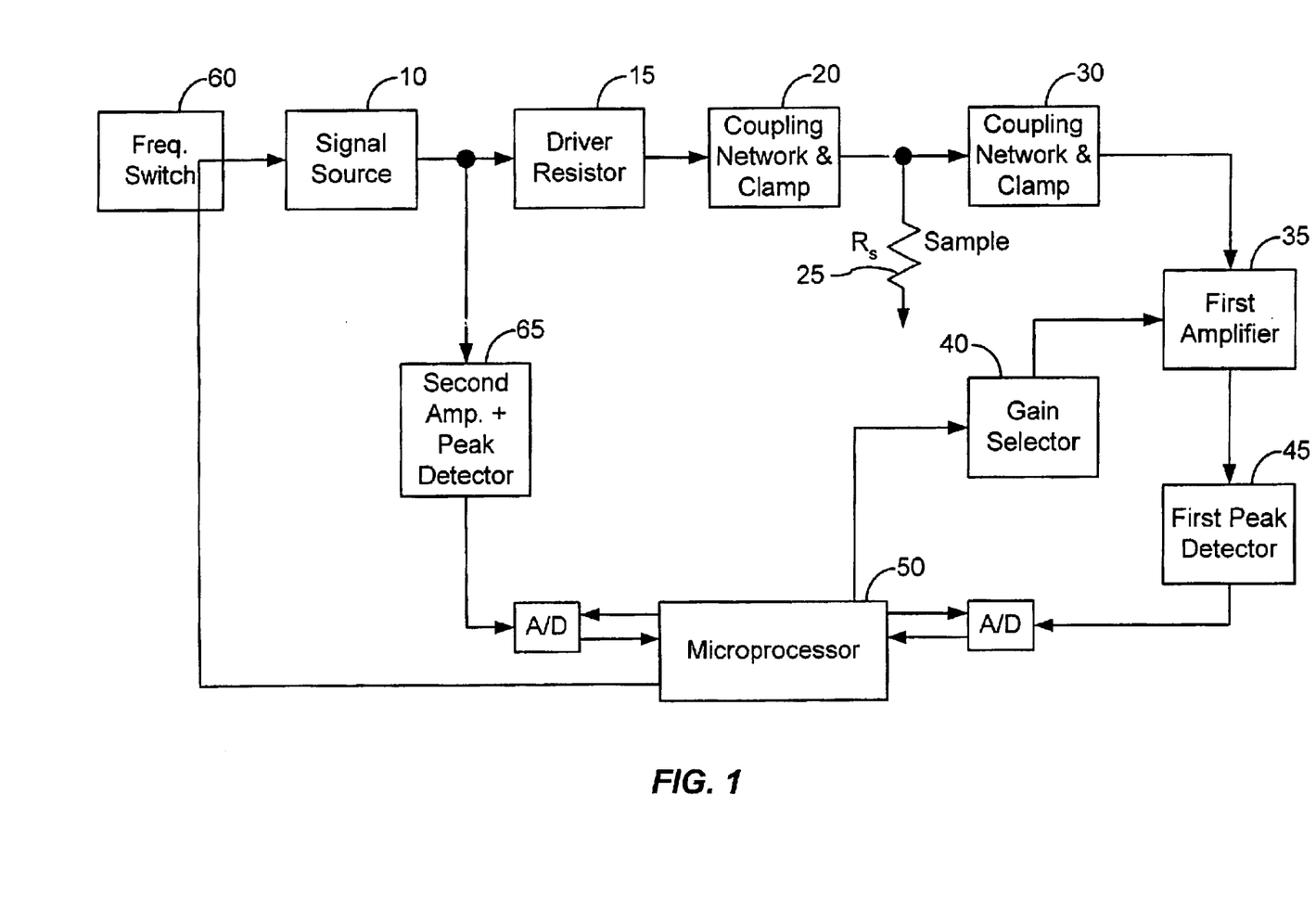
FIG. 1 illustrates a block diagram of a resistance measurement system with a hardware connection to an external sample according to an embodiment of the present invention.

FIG. 1 illustrates a block diagram of a resistance measurement system with a hardware connection to an external sample according to an embodiment of the present invention. As shown, a signal generator 10 generates a source signal. In one embodiment, the signal generator produces a sinusoidal signal of 20–25 KHz which ultimately passes current through the driver resistor 15, and the coupling network 20 (plus clamp for protection) to the sample 25. Depending on sample resistance, a voltage is produced across the sample indicative of the sample resistance, Rs. This voltage is passed through a second coupling network 30 (and clamp), a first amplifier 35 (with optional gain selector 40), and a first peak detector 45. The coupling circuits and the clamp protect against high voltages that appear across the sample. The peak value of the sample voltage is converted to a digital signal by one of the A/D channels of the microprocessor 50.

In one embodiment, the source signal is also amplified and the peak detected by a second amplifier and peak detector 65 to provide a reference signal. This reference signal is converted to a digital signal by a second A/D channel of the microprocessor 50. The addition of the reference signal provided to the microprocessor is an improvement over the prior resistance-measuring systems as the reference allows the microprocessor 50 to compensate for changes in the source signal amplitude. The microprocessor 50 is also configured to monitor and alter the frequency of the source signal via frequency switch 60 (this can also change the amplitude of the source signal).

The block diagram shown in FIG. 1 is generally similar to the previous systems with the exception of the addition of the frequency switch 60 and the second amp and peak detector 65. The sample circuit can be simplified to that shown in FIG. 2.

Figure 2:
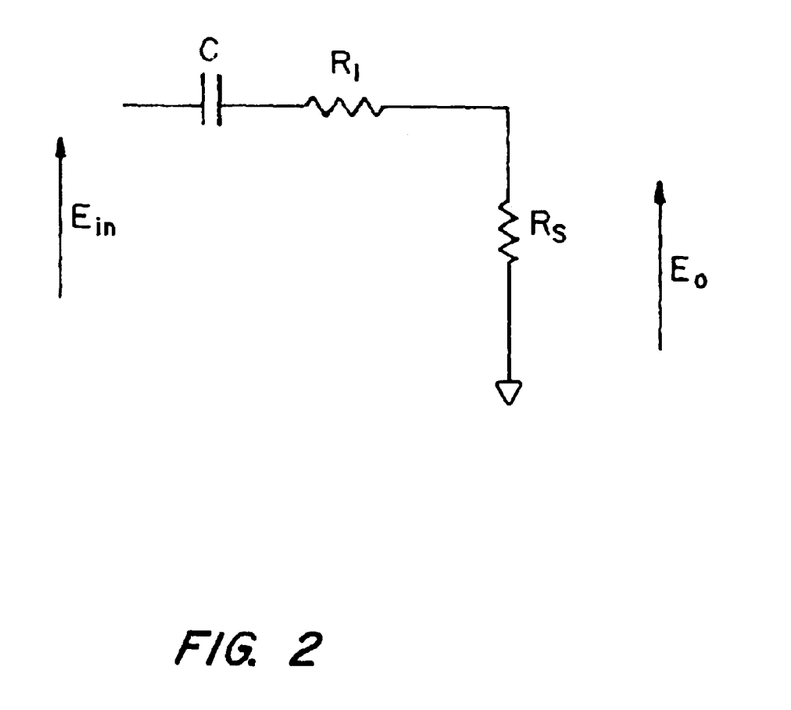
FIG. 2 illustrates a simplified view of a portion of the sample circuit as shown in FIG. 1.

One problem solved by the present invention is the effect of the change of the coupling capacitor, C, with temperature (and other capacitor changes such as aging). In the prior systems, the capacitor could change its value thereby causing an error in the resistance measurement. However, the system had a lower expectation for resistance-measurement accuracy. As temperature changes, the reactance of C changes, affecting Eo. According to one embodiment of the present invention, a method of measuring the voltage across the load, Rs, at two different frequencies is provided. The use of two frequencies is another important improvement over the prior resistance-measuring circuits. In certain aspects, frequencies are chosen such that the sample resistance, Rs, remains substantially constant at the two frequencies (e.g., 20 KHz and 25 KHz, although it should be appreciated that any other frequencies may be used). However, when the reactance of the capacitor changes at the separate frequencies, two equations can be generated to solve for the two unknowns (actual C and sample resistance, Rs) as follows:

---

Assume that Eo1 = Eo at frequency f1
Assume that Eo2 = Eo at frequency f2
Eo1 = RsEin/((½πf1C) + R1 + Rs)   E02 = RsEin/((½πf2C) + R1 + Rs)
Rs = (Eo1/(Ein−Eo1))((½πf1C) + R1)   Rs = (Eo2/(Ein−Eo2))((½πf2C) + R1)
Then C = [(Eo2/(Ein−Eo2)(2πf2)) − Eo1/(Ein−Eo1)(2πf1)]/
   {[(R1Eo1)/(Ein−Eo1)]−(R1Eo2/(Ein−Eo2)},
And if K1 = Ein−Eo1, K2 = Ein−Eo2, K3 = Eo1/K1, K4 = E02/K2,
Then Rs = [K3R1f2(K3 + K4)/(K4f1 + K3f2)] + K3(R1)$^2$/f1

---

Hence, Rs can be found independent of the change in C if two different frequencies are used. Preferably, microprocessor 50 is configured to automatically determine Rs, although appropriate data signals may be sent to another processing unit.

Figures 3, 3B:
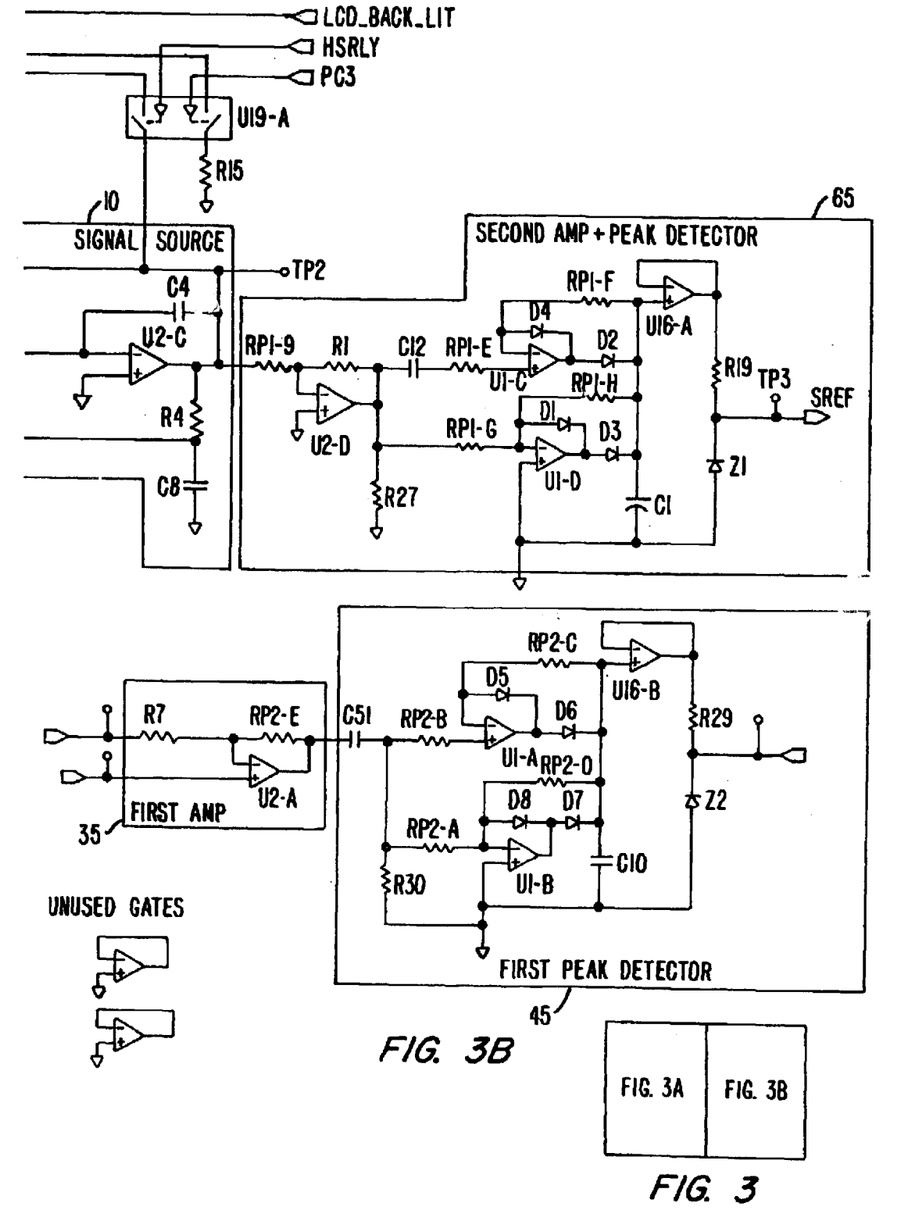
FIGS. 3 and 4 illustrate details of the circuit elements of FIG. 1 according to an embodiment of the present invention.
Figure 3A:
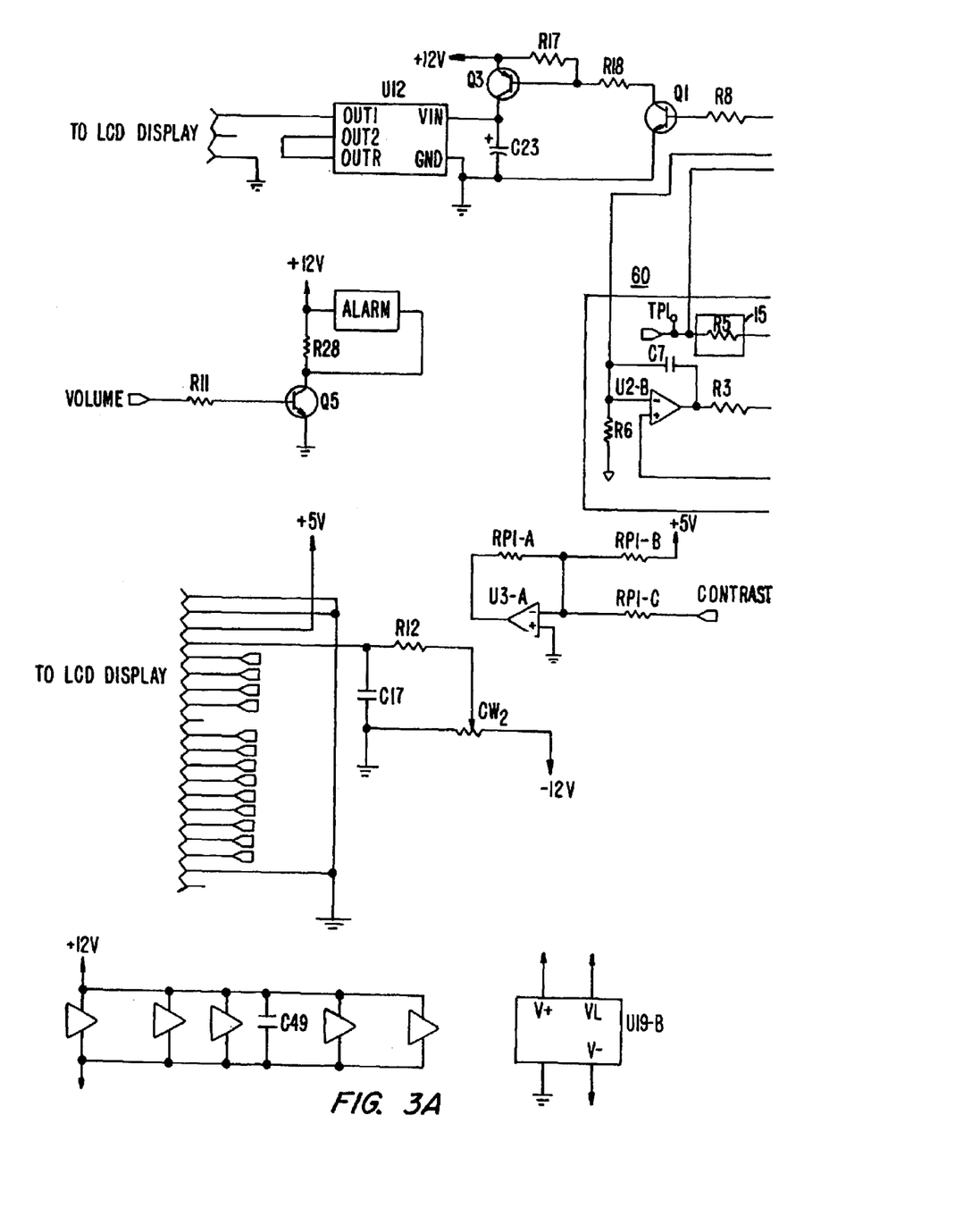
Figure 4:
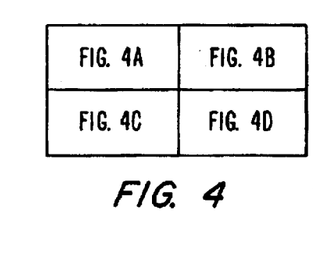
Figure 4A:
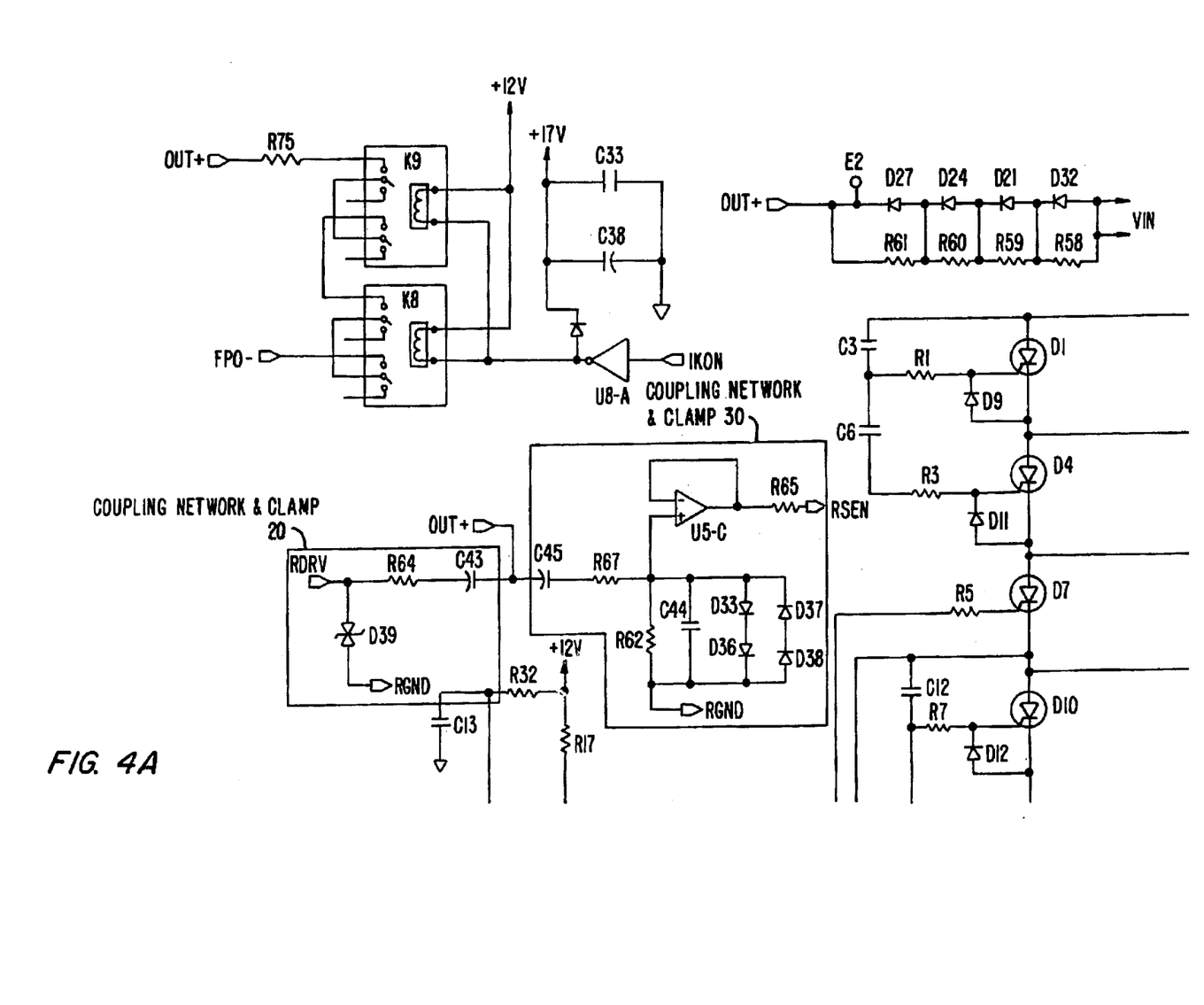
Figure 4B:
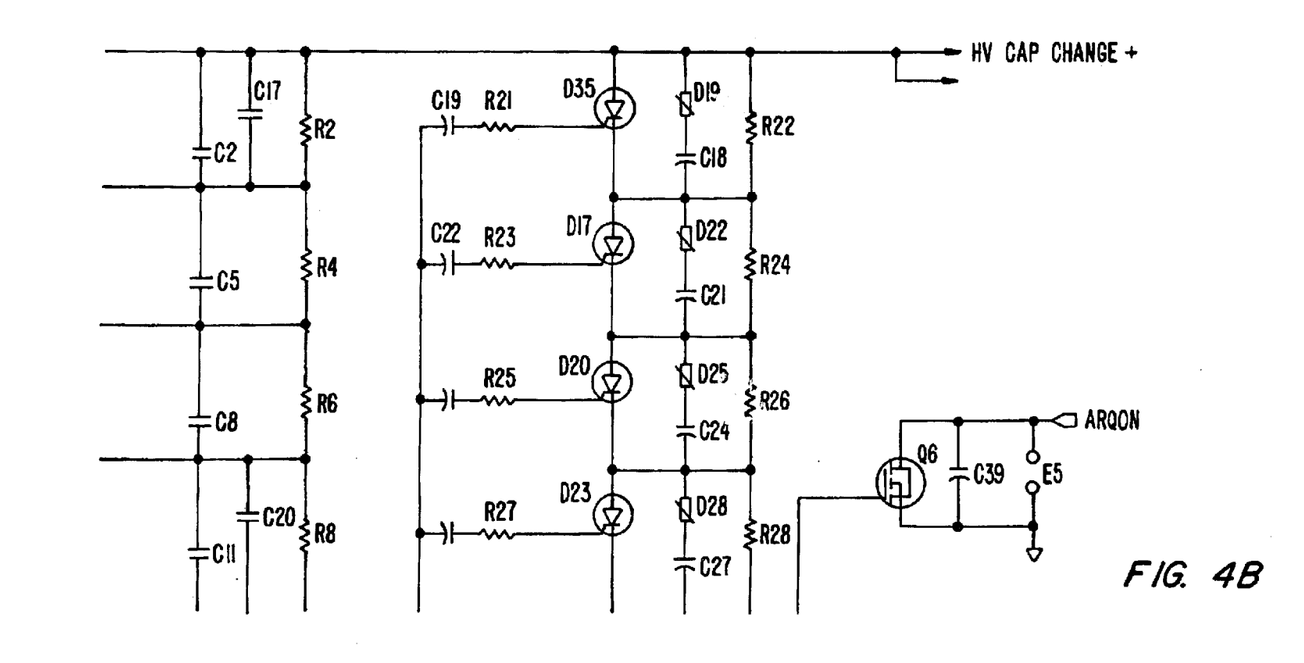
Figure 4C:
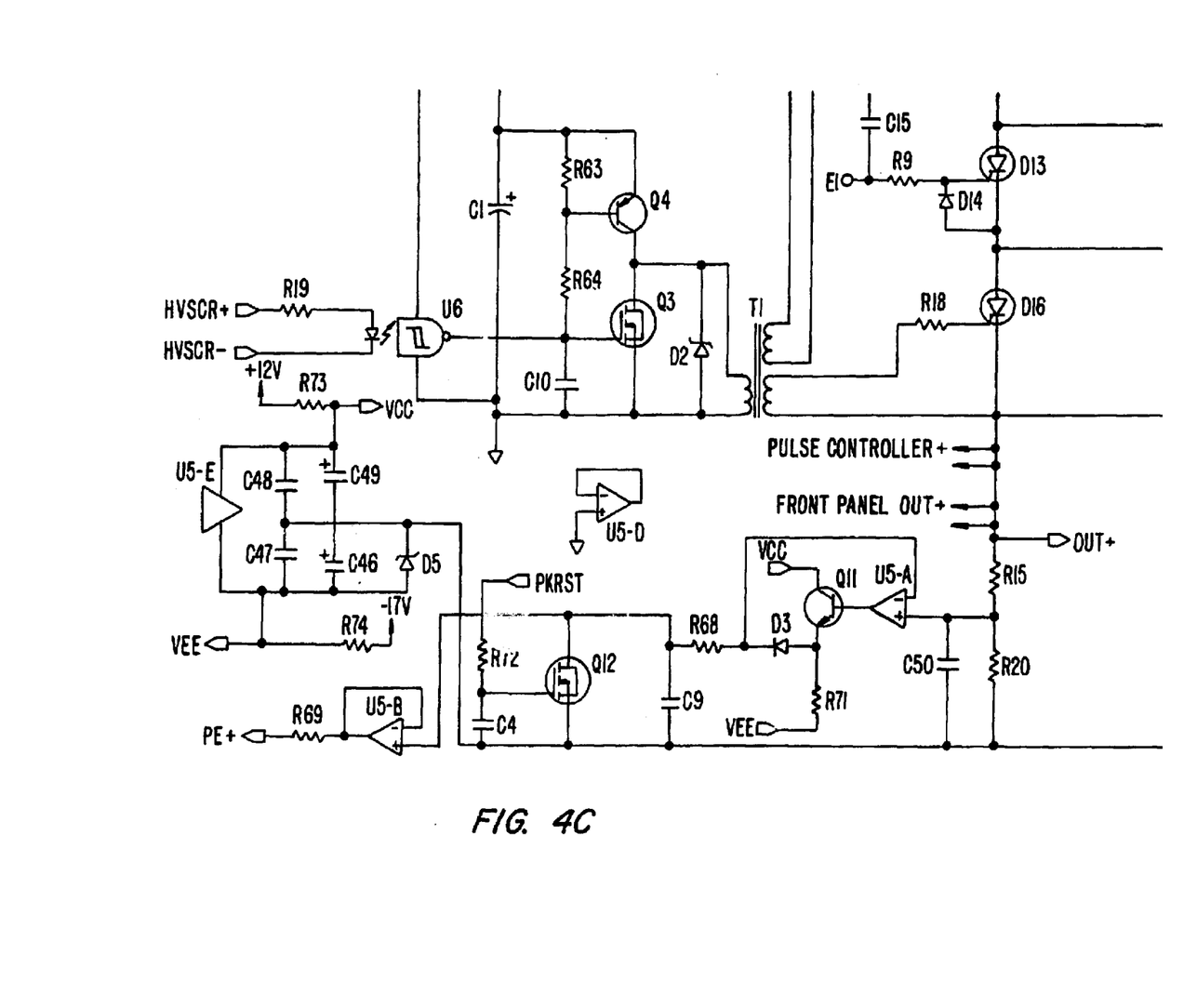
Figure 4D:
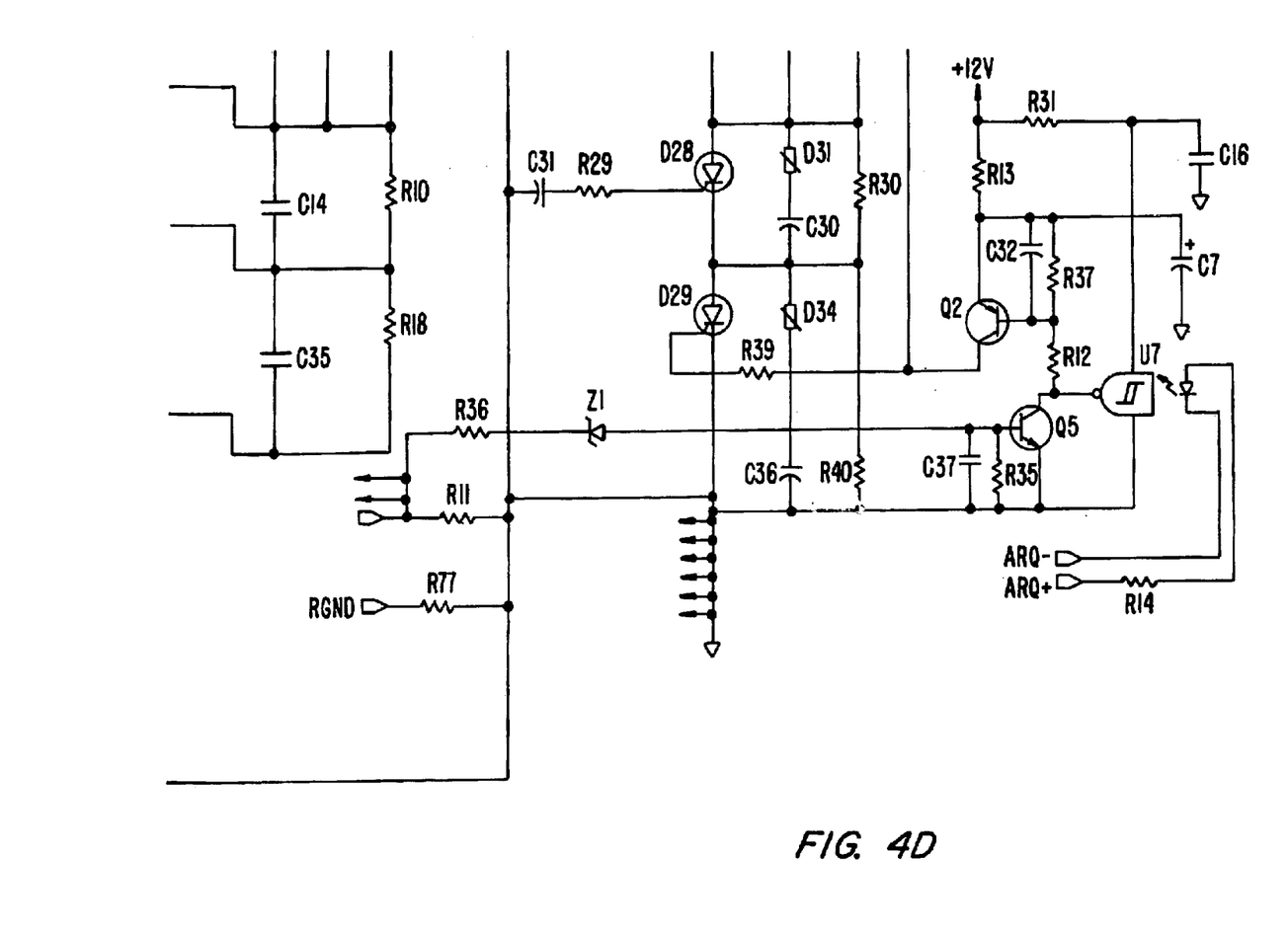

FIGS. 3 and 4 illustrate details of the circuit elements of FIG. 1 according to one specific embodiment of the present invention. It should be appreciated that variations in the circuit element values and design and alternate circuit elements and arrangements may be used.

Figure 5:
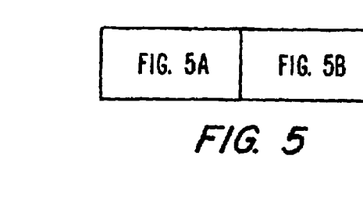
FIGS. 5 and 6 are schematic illustrations of a resistance control system according to an embodiment of the present invention.
Figure 5A:
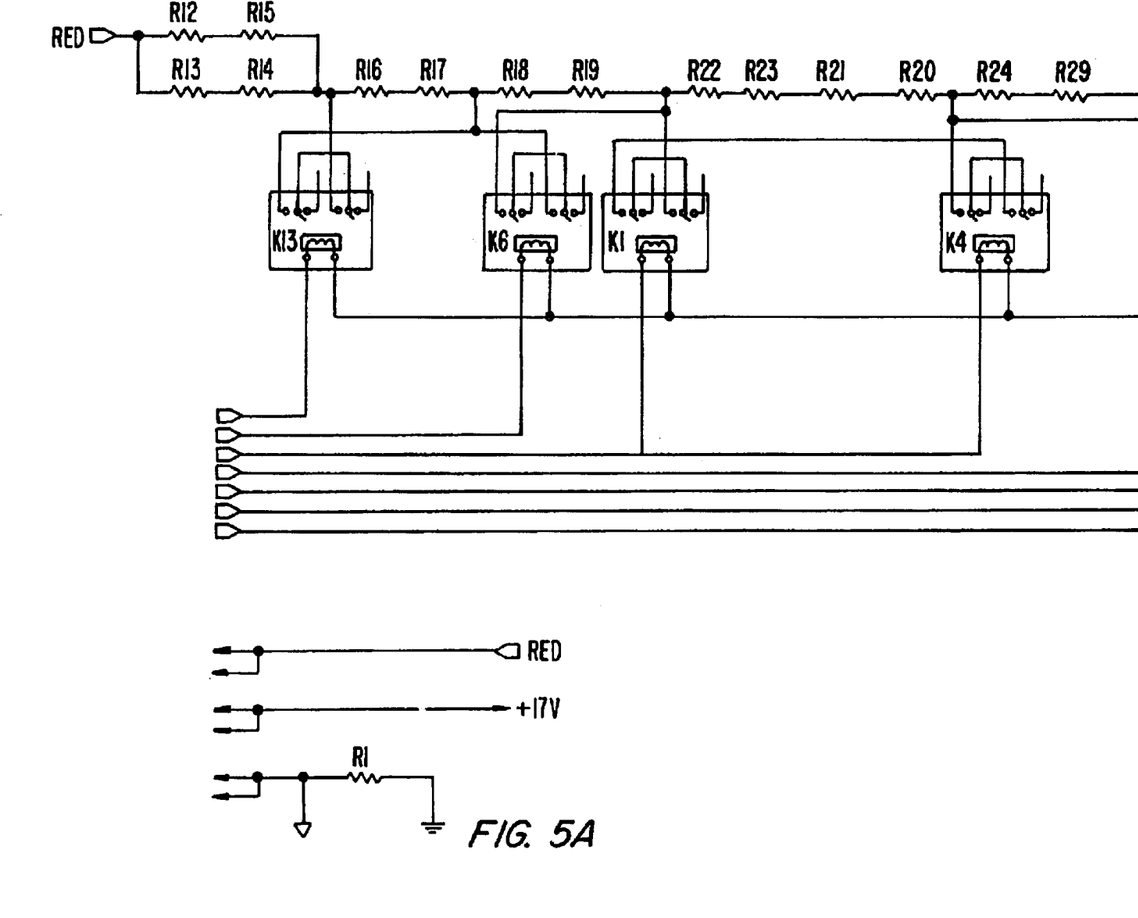
Figure 5B:
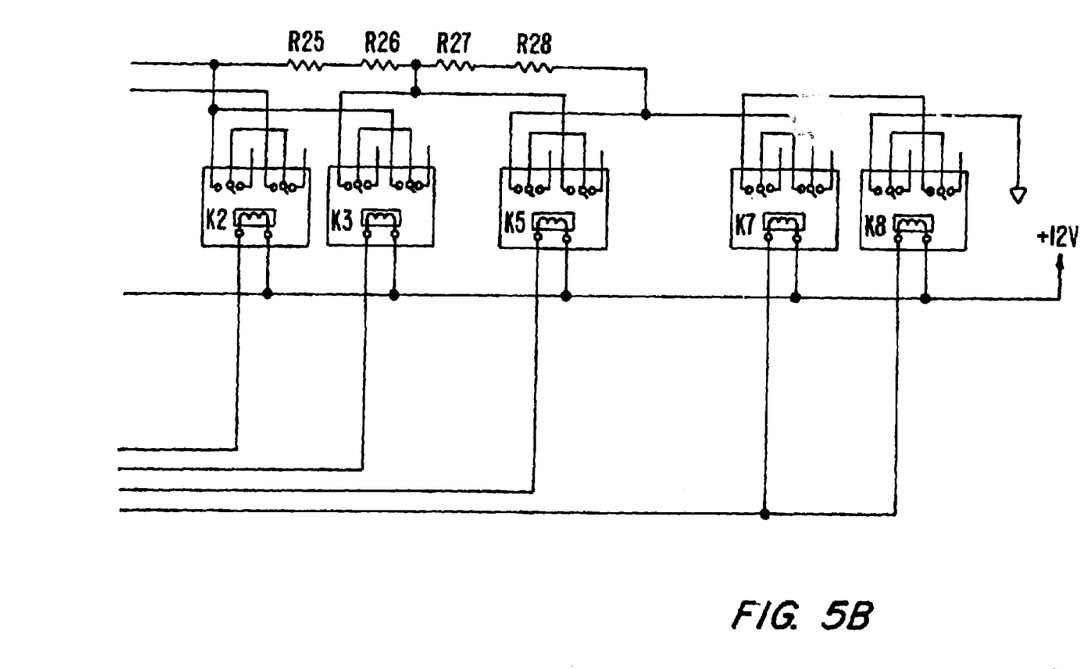
Figures 6, 6B:
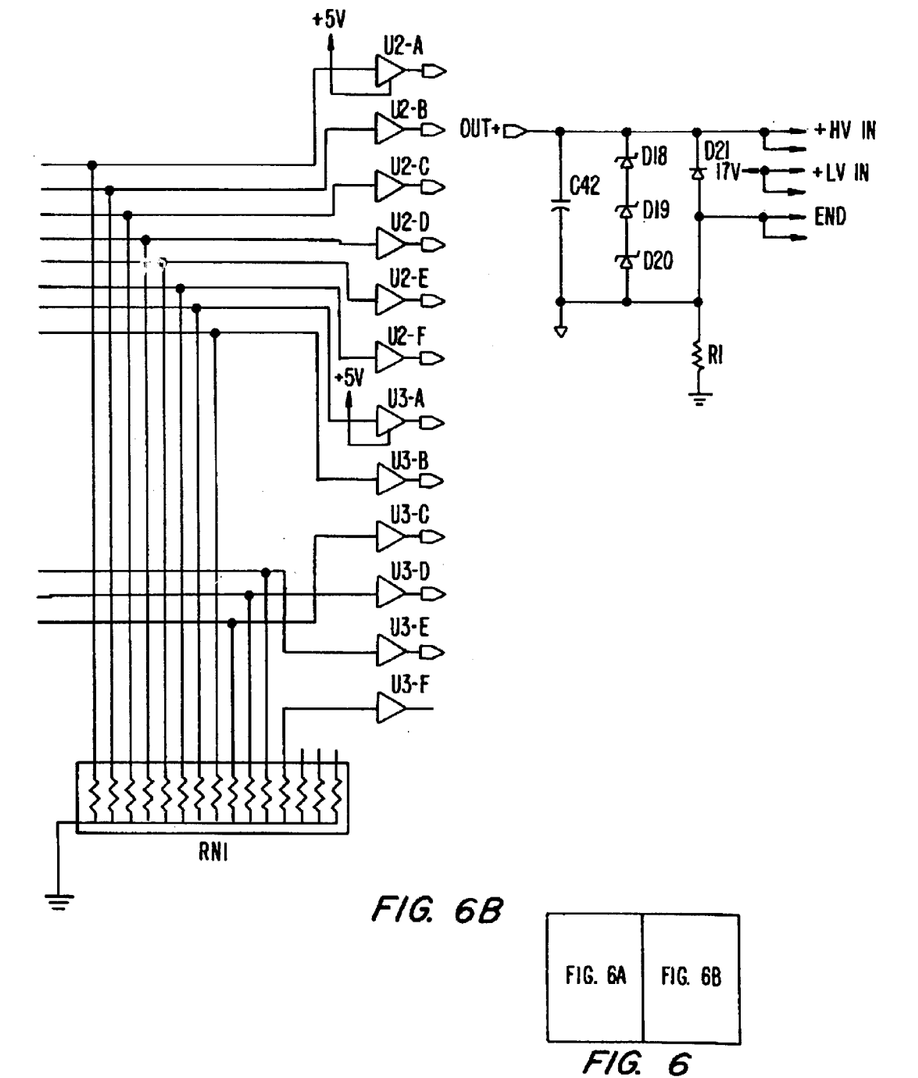
Figure 6A:
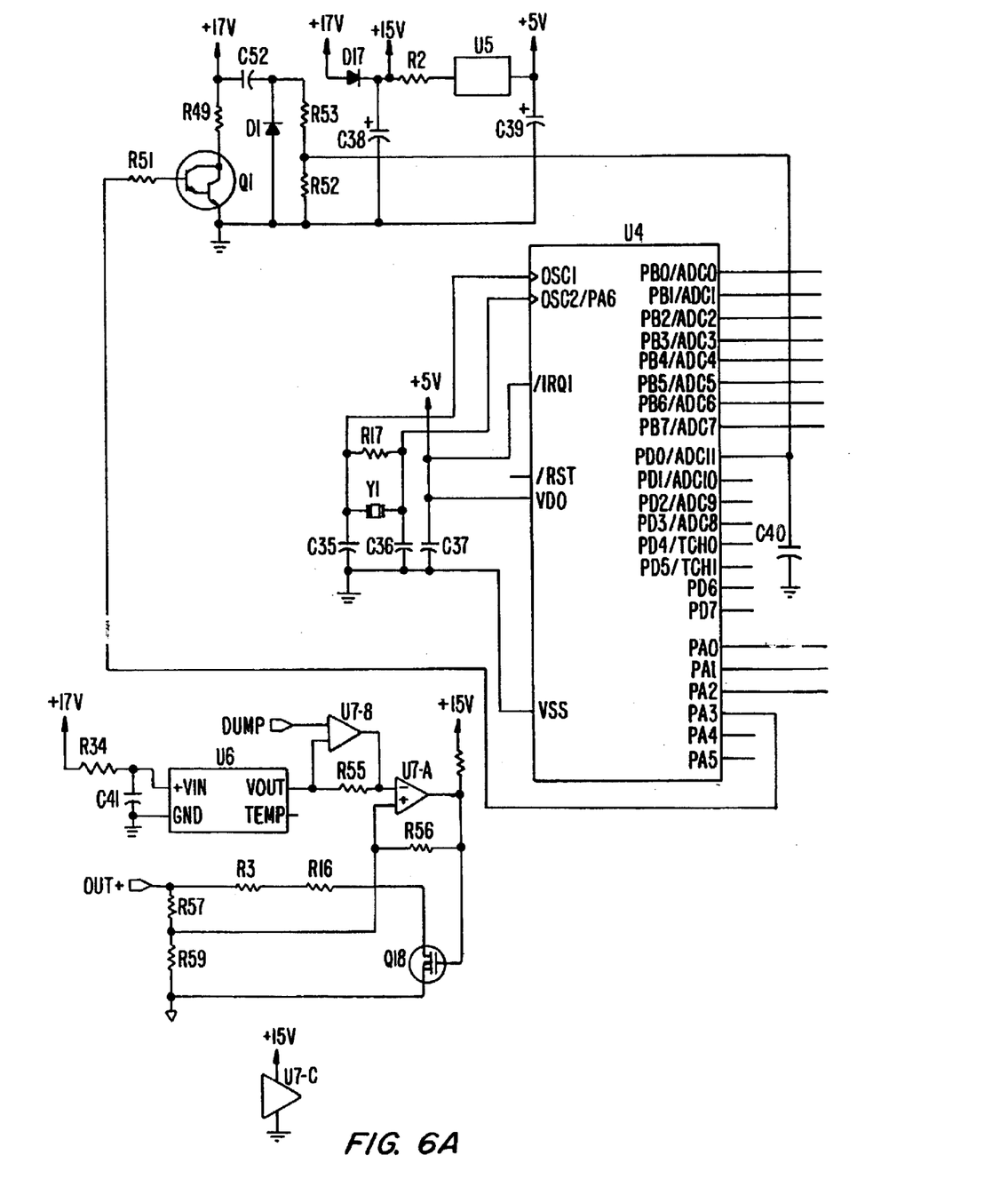

According to an embodiment of the present invention, an electroporation system (electroporator) includes a resistance control system configured to measure the resistance of the sample and to automatically couple an internal resistor in parallel with the sample so as to achieve a desired time constant. FIGS. 5 and 6 are schematic illustrations of a resistance control system according to a specific embodiment of the present invention. It should be appreciated that variations in the circuit element values and design and alternate circuit elements and arrangements may be used. The resistance control system, in one embodiment as shown, is configured to switch-in resistors in a range of 50 to 1000 (and infinity) ohms, in 50 ohm increments. It should be appreciated that other resistance ranges and increments may be implemented.

In operation, an operator selects or inputs a desired time constant. The system then measures the resistance of the sample (e.g., as described above) before selection of a parallel resistance. The system also automatically selects a capacitance from a range of capacitors. For example, in one embodiment as shown in FIG. 6, low voltage capacitors with a total capacitance ranging from 25 mfd to 3375 mfd with 25 mfd increments may be selected, or high voltage capacitors of 50, 25 and 10 mfd may be selected. It should be appreciated that other capacitance ranges and increments may be implemented. U.S. Pat. Nos. 5,729,426, 5,656,926 and 5,642,035 disclose systems and methods for electronically controlling the selection of capacitors.

If, for example, the operator selects 5.0 msec as the time constant, and the system measures a sample resistance of 200 ohms, the system need only select a 25 mfd capacitance. However, if the operator selects 7.0 msec as the time constant for the same 200 ohm sample load, the system automatically selects a higher capacitance, e.g., 50 mfd. However, 50 mfd would produce a 10 msec pulse duration (time constant). Hence, the system reduces the time constant by switching in a parallel resistor. The system determines/calculates the required resistance using the equation:

$$R=(R1 \times Rs)/(R1+Rs),$$

where R1 is the desired parallel add-on resistance, and Rs is the (determined) sample resistance. Since the desired time constant is 7 msec=RC, and C=50 mfd, R=7 msec/50 mfd=140 ohms. Thus, $140=(R1 \times 200)/(R1+200)$. Solving for R1: R1 is approximately 467 ohms. Because the possible R1s are in 50 ohm increments in the present example, the closest parallel add-on resistance is 450 ohms, which provides an actual time constant of 6.92 msec, close to the desired 7 msec. In one embodiment, the system displays the actual time constant that is achieved (e.g., "6.92 msec").

In one embodiment, the resistance is maximized. In this embodiment, the system selects the minimum capacitance that can, without a selected parallel add-on resistance, achieve a time constant slightly greater than the desired time constant. It is then possible to maximize the selected value of the parallel add-on resistance. This minimizes the wasted energy in the add-on resistance. In another embodiment, the capacitance is maximized.

The present invention is particularly useful in the automatic electroporation optimization system as disclosed in copending U.S. patent application Ser. No. 10/313,893, filed on even date herewith, claiming priority to U.S. Provisional Patent Application Serial No. 60/337,095, filed Dec. 6, 2001, both titled "AUTOMATIC ELECTROPORATION OPTIMIZATION SYSTEM", the contents of which are both hereby incorporated by reference in their entirety. For example, in such a system, implementation of the present invention allows for the electroporation system to automatically select the optimum capacitance and resistance values to be added in for each of a series of electroporation pulses.

The present invention can also be utilized in electrofusion experiment, for example using the teachings of copending U.S. Patent Application Serial No. 10/313,958, filed on even date herewith, claiming priority to U.S. Provisional Patent Application Serial No. 60/337,097, filed Dec. 6, 2001, both titled "ELECTROPORATION CUVETTE INSERT FOR FACILITATING MEMBRANE0BASED FUSION", the contents of which are both hereby incorporated by reference in their entirety.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A method of applying an electrical pulse to a sample for a desired duration in an electroporation system, the method comprising:
    identifying a desired pulse duration;
    automatically measuring the resistance Rs of the sample;
    automatically selecting a capacitance C to be placed in series with the sample; and
    automatically determining a resistance R2 to be placed in parallel with the sample such that a time constant $T=C \times R$ is substantially equal to the desired pulse duration, wherein $R=(Rs \times R2)/(Rs+R2)$.

2. The method of claim 1, wherein identifying includes receiving a pulse duration as user input.

3. The method of claim 1, wherein selecting a capacitance C includes selecting from a range of capacitance values a minimum capacitance value that achieves a time constant slightly greater than the desired time constant.

4. The method of claim 1, further including selecting from a range of resistance values a resistance value that is closest to the determined resistance R2.

5. The method of claim 1, further including automatically selecting and coupling a capacitor and a resistor to the sample from a plurality of capacitors and resistors, said capacitor and resistor having values substantially equal to the selected capacitance C and determined resistance R2.

6. The method of claim 1, wherein automatically measuring the resistance Rs of the sample includes:
    applying a first input signal to the sample across a coupling capacitor and a drive resistor circuit, the first input signal having an input voltage Ein at a first frequency f1, said drive resistor circuit having a resistance R1;
    measuring the voltage E1 across the sample at said first frequency;
    applying a second input signal to the sample across the drive resistor circuit, the second input signal having the input voltage Ein at a second frequency f2;
    measuring the voltage E2 across the sample at said second frequency;

determining the sample resistance Rs using Ein and the measured values E1 and E2 without using the capacitance of the coupling capacitor.

7. A method of automatically determining the resistance of a sample in an electroporation system, comprising:
applying a first input signal to the sample across a coupling capacitor and a drive resistor circuit, the first input signal having an input voltage Ein at a first frequency f1, said drive resistor circuit having a resistance R1;
measuring the voltage E1 across the sample at said first frequency;
applying a second input signal to the sample across the drive resistor circuit, the second input signal having the input voltage Ein at a second frequency f2;
measuring the voltage E2 across the sample at said second frequency; and
determining the sample resistance Rs using Ein and the measured values E1 and E2 without using the capacitance of the coupling capacitor.

8. The method of claim 7, wherein determining includes determining the sample resistance Rs using only the resistance of the drive circuit R1, the input voltage Ein, the measured values E1 and E2 and the frequencies f1 and f2.

9. The method of claim 7, wherein determining includes determining the sample resistance Rs using the equation:

$$Rs=[K3R1f2(K3+K4)/(K4f1+K3f2)]+K3(R1)2/f1,$$

where $K1=Ein-E1$, $K2=Ein-E2$, $K3=E1/K1$, $K4=E2/K2$.

10. A method of automatically determining the resistance of a sample in an electroporation system, comprising:
applying a first input signal to the sample across a coupling capacitor and drive resistor circuit, the first input signal having an input voltage Ein at a first frequency f1, said drive resistor circuit having a resistance R1;
taking a first measurement of the voltage, E1, across the sample at said first frequency;
applying a second input signal to the sample across the coupling capacitor and drive resistor circuit, the second input signal having the input voltage Ein at a second frequency f2;
taking a second measurement of the voltage, E2, across the sample at said second frequency; and
determining the sample resistance Rs using Ein and the measured values E1 and E2 such that Rs is determined independent of any changes in the capacitance C of the coupling capacitor between the first and second measurements.

11. A system for applying an electrical pulse to a sample for a desired duration in an electroporation system, the system comprising:
means for identifying a desired pulse duration;
means for automatically measuring the resistance Rs of the sample;
means for automatically selecting a capacitance C to be placed in series with the sample; and
means for automatically determining a resistance R2 to be placed in parallel with the sample such that a time constant T=C×R is substantially equal to the desired pulse duration, wherein R=(Rs×R2)/(Rs+R2).

12. The system of claim 11, wherein the means for automatically measuring the resistance Rs of the sample includes:
means for applying a first input signal to the sample across a coupling capacitor and a drive resistor circuit, the first input signal having an input voltage Ein at a first frequency f1, said drive resistor circuit having a resistance R1;
means for measuring the voltage E1 across the sample at said first frequency;
means for applying a second input signal to the sample across the drive resistor circuit, the second input signal having the input voltage Ein at a second frequency f2;
means for measuring the voltage E2 across the sample at said second frequency; and
means for determining the sample resistance Rs using Ein and the measured values E1 and E2 without using the capacitance of the coupling capacitor.

13. A system for automatically determining the resistance of a sample in an electroporation system, comprising:
means for applying a first input signal to the sample across a coupling capacitor and a drive resistor circuit, the first input signal having an input voltage Ein at a first frequency f1, said drive resistor circuit having a resistance R1;
means for measuring the voltage E1 across the sample at said first frequency;
means for applying a second input signal to the sample across the drive resistor circuit, the second input signal having the input voltage Ein at a second frequency f2;
means for measuring the voltage E2 across the sample at said second frequency; and
means for determining the sample resistance Rs using Ein and the measured values E1 and E2 without using the capacitance of the coupling capacitor.

14. A circuit arrangement in an electroporation system configured to determine the resistance of a sample, the arrangement comprising:
a signal source for providing a sinusoidal voltage signal to a sample across a coupling capacitor and drive resistor;
a frequency switch coupled to the signal source, the switch configured to adjust the frequency of the voltage signal applied by the signal source;
a microprocessor coupled to the frequency switch, an output of the signal source and the sample, wherein the microprocessor controls the signal source via the frequency switch to apply a first voltage signal to the sample at a first frequency and a second voltage signal to the sample at a second frequency, the first and second voltage signals having substantially the same voltage amplitude,
wherein the microprocessor is configured to determine the sample resistance Rs based on the applied voltage amplitude of the first and second voltage signals and on the detected voltage levels across the sample at the first and second frequencies.

15. The system of claim 14, wherein the microprocessor is coupled to the output of the signal source through an amplifier circuit and an AD converter module so that the microprocessor receives as a reference signal the output of the signal source.

16. The system of claim 14, wherein the microprocessor is coupled to the sample through an amplifier circuit and an AD converter module.

17. The system of claim 14, wherein the microprocessor determines the sample resistance Rs by applying an algorithm:

$$Rs=[K3R1f2(K3+K4)/(K4f1+K3f2)]+K3(R1)2/f1,$$

where $K1=Ein-E1$, $K2=Ein-E2$, $K3=E1/K1$, $K4=E2/K2$, and where Ein is the amplitude of the applied voltage signals, E1 is the amplitude of the voltage measured across the sample at the first frequency, E2 is the amplitude of the voltage measured across the sample at the second frequency, R1 is the resistance of the drive resistor, f1 is the first frequency and f2 is the second frequency.

* * * * *